(12) United States Patent
Chen et al.

(10) Patent No.: US 10,082,488 B2
(45) Date of Patent: Sep. 25, 2018

(54) TIME GAIN COMPENSATION CIRCUIT AND RELATED APPARATUS AND METHODS

(71) Applicant: Butterfly Network, Inc., Guilford, CT (US)

(72) Inventors: Kailiang Chen, Guilford, CT (US); Tyler S. Ralston, Clinton, CT (US)

(73) Assignee: Butterfly Network, Inc., Guilford, CT (US)

( * ) Notice: Subject to any disclaimer, the term of this patent is extended or adjusted under 35 U.S.C. 154(b) by 182 days.

(21) Appl. No.: 14/957,443

(22) Filed: Dec. 2, 2015

(65) Prior Publication Data

US 2017/0160239 A1 Jun. 8, 2017

(51) Int. Cl.
*G01N 29/11* (2006.01)
*G01N 29/06* (2006.01)
*G01N 29/44* (2006.01)

(52) U.S. Cl.
CPC ......... *G01N 29/11* (2013.01); *G01N 29/0654* (2013.01); *G01N 29/44* (2013.01); *G01N 2291/015* (2013.01); *G01N 2291/02475* (2013.01)

(58) Field of Classification Search
CPC ........ G01N 29/11; G01N 29/00; G01N 29/04; G01N 29/046; G01N 29/07; G01N 29/09; G01N 29/12; G01N 29/14; G01N 29/22; G01N 29/24; G01N 29/34; G01N 29/346; G01N 29/348; G01N 29/36; G01N 29/38; G01N 29/44
See application file for complete search history.

(56) References Cited

U.S. PATENT DOCUMENTS

| 4,810,949 | A | * | 3/1989 | Schiemenz | G06J 1/00 |
| | | | | | 323/354 |
| 4,852,576 | A | | 8/1989 | Inbar et al. | |
| 5,233,305 | A | * | 8/1993 | Nishizawa | G01R 31/027 |
| | | | | | 324/546 |
| 5,263,092 | A | * | 11/1993 | Jang | H03G 3/001 |
| | | | | | 381/104 |
| 5,351,030 | A | * | 9/1994 | Kobayashi | H03H 7/24 |
| | | | | | 333/81 R |

(Continued)

FOREIGN PATENT DOCUMENTS

| CN | 103607130 A | 2/2014 |
| TW | 201445554 A | 12/2014 |

OTHER PUBLICATIONS

International Search Report and Written Opinion dated Mar. 27, 2017 for Application No. PCT/US2016/064322.

(Continued)

*Primary Examiner* — Harshad R Patel
(74) *Attorney, Agent, or Firm* — Wolf, Greenfield & Sacks, P.C.

(57) ABSTRACT

An ultrasound device, including a profile generator, an encoder configured to receive a profile signal from the profile generator, and an attenuator configured to receive a signal representing an output of an ultrasound sensor and coupled to the encoder to receive a control signal from the encoder, the attenuator including a plurality of attenuator stages, the attenuator configured to produce an output signal that is an attenuated version of the input signal.

22 Claims, 7 Drawing Sheets

(56) References Cited

U.S. PATENT DOCUMENTS

| | | | |
|---|---|---|---|
| 5,408,199 A * | 4/1995 | Nagano | H03G 3/001 330/129 |
| 5,482,044 A | 1/1996 | Lin et al. | |
| 5,757,220 A * | 5/1998 | Murden | H03H 11/24 327/306 |
| 5,955,670 A * | 9/1999 | Goodman | F16C 33/6625 340/605 |
| 5,963,882 A * | 10/1999 | Viertl | G01N 29/265 702/104 |
| 6,163,288 A * | 12/2000 | Yoshizawa | H03M 1/682 341/144 |
| 6,229,375 B1 | 5/2001 | Koen | |
| 6,693,491 B1 * | 2/2004 | Delano | H03G 1/0088 330/254 |
| 6,828,873 B2 * | 12/2004 | Ludwig | H03H 11/245 327/308 |
| 7,253,700 B1 * | 8/2007 | Chiu | H03G 1/0088 327/308 |
| 7,313,053 B2 | 12/2007 | Wodnicki | |
| 8,076,995 B2 * | 12/2011 | Chiu | H03H 7/24 327/308 |
| 8,330,536 B1 | 12/2012 | Quinn | |
| 8,514,007 B1 * | 8/2013 | Ahmed | G06G 7/10 327/355 |
| 8,653,890 B1 * | 2/2014 | Ahmed | H03F 1/0222 330/107 |
| 8,852,103 B2 | 10/2014 | Rothberg et al. | |
| 9,100,046 B2 * | 8/2015 | Granger-Jones | H03M 1/682 |
| 9,229,097 B2 | 1/2016 | Rothberg et al. | |
| 9,444,432 B2 * | 9/2016 | Shrivastava | H01F 38/14 |
| 9,473,136 B1 | 10/2016 | Chen et al. | |
| 9,492,144 B1 | 11/2016 | Chen et al. | |
| 9,543,925 B2 * | 1/2017 | Hau | H03H 7/38 |
| 9,705,518 B2 | 7/2017 | Chen et al. | |
| 2002/0180520 A1 | 12/2002 | Ueno et al. | |
| 2007/0030070 A1 | 2/2007 | Brueske et al. | |
| 2007/0069934 A1 * | 3/2007 | Mills | H04M 15/00 341/144 |
| 2007/0090877 A1 * | 4/2007 | Bagheri | H03F 1/48 330/254 |
| 2007/0242567 A1 | 10/2007 | Daft et al. | |
| 2009/0250729 A1 | 10/2009 | Lemmerhirt et al. | |
| 2010/0063399 A1 | 3/2010 | Walker et al. | |
| 2010/0152587 A1 | 6/2010 | Haider et al. | |
| 2010/0164656 A1 * | 7/2010 | Chiu | H03H 7/24 333/81 R |
| 2010/0317972 A1 | 12/2010 | Baumgartner et al. | |
| 2011/0133841 A1 | 6/2011 | Shifrin | |
| 2011/0148682 A1 | 6/2011 | Rigby et al. | |
| 2013/0043962 A1 * | 2/2013 | Granger-Jones | H03M 1/682 333/81 R |
| 2013/0120061 A1 * | 5/2013 | van der Zanden | H03F 1/0288 330/124 R |
| 2014/0077874 A1 * | 3/2014 | Ahmed | H03F 3/211 330/124 R |
| 2014/0114190 A1 | 4/2014 | Chiang et al. | |
| 2014/0184330 A1 | 7/2014 | Dusad | |
| 2014/0288428 A1 | 9/2014 | Rothberg et al. | |
| 2014/0293738 A1 | 10/2014 | Yoshioka | |
| 2015/0032002 A1 | 1/2015 | Rothberg et al. | |
| 2015/0091646 A1 | 4/2015 | Shifrin | |
| 2015/0280662 A1 | 10/2015 | Nimran et al. | |
| 2015/0297193 A1 | 10/2015 | Rothberg et al. | |
| 2015/0374335 A1 | 12/2015 | Brown et al. | |
| 2017/0160387 A1 | 6/2017 | Chen et al. | |
| 2017/0160388 A1 | 6/2017 | Chen et al. | |
| 2017/0163225 A1 | 6/2017 | Chen et al. | |
| 2017/0163276 A1 | 6/2017 | Chen et al. | |
| 2017/0202541 A1 | 7/2017 | Ralston | |
| 2017/0264307 A1 | 9/2017 | Chen et al. | |
| 2017/0307739 A1 | 10/2017 | Chen et al. | |

OTHER PUBLICATIONS

Agarwal et al., Single-Chip Solution for Ultrasound Imaging Systems: Initial Results. 2007 IEEE Ultrasonics Symposium. Oct. 1, 2007;1563-6.

Chen et al., Ultrasonic Imaging Front-End Design for CMUT: A 3-Level 30Vpp Pulse-Shaping Pulser with Improved Efficiency and a Noise-Optimized Receiver. IEEE Asian Solid-State Circuits Conference. Nov. 12-14, 2012;173-6.

Cheng et al., An Efficient Electrical Addressing Method Using Through-Wafer Vias for Two-Dimensional Ultrasonic Arrays. 2000 IEEE Ultrasonics Symposium. 2000;2:1179-82.

Cheng et al., CMUT-in-CMOS ultrasonic transducer arrays with on-chip electronics. Transducers 2009. IEEE. Jun. 21, 2009;1222-5.

Cheng et al., Electrical Through-Wafer Interconnects with Sub-PicoFarad Parasitic Capacitance. 2001 Microelectromechan Syst Conf. Aug. 24, 2001;18-21.

Daft et al., 5F-3 A Matrix Transducer Design with Improved Image Quality and Acquisition Rate. 2007 IEEE Ultrasonics Symposium. Oct. 1, 2007;411-5.

Daft et al., Microfabricated Ultrasonic Transducers Monolithically Integrated with High Voltage Electronics. 2004 IEEE Ultrasonics Symposium. Aug. 23, 2004;1:493-6.

Gurun et al., Front-end CMOS electronics for monolithic integration with CMUT arrays: circuit design and initial experimental results. Proc Ultrason Symp. 2008;390-3.

Khuri-Yakub et al., Miniaturized Ultrasound Imaging Probes Enabled by CMUT Arrays with Integrated Frontend Electronic Circuits. Conf Proc IEEE Eng Med Biol Soc. 2010;1:5987-90. doi:10.1109/IEMBS.2010.5627580. Epub Dec. 6, 2010. 13 pages.

Kim et al., Design and Test of a Fully Controllable 64x128 2-D CMUT Array Integrated with Reconfigurable Frontend ASICs for Volumetric Ultrasound Imaging. IEEE. International Ultrasonics Symposium Proceedings. Oct. 7-10, 2012;77-80. doi: 10.1109/ULTSYM.2012.0019.

Jiajian, Time-Gain-Compensation Amplifier for Ultrasonic Echo Signal Processing. Electronics Instrumentation Laboratory, Department of Microelectronics. Delft University of Technology. Feb. 2010 81 pages.

Tang et al., Automatic Time Gain Compensation in Ultrasound Imaging System. 3rd International Conference on Bioinformatics and Biomedical Engineering. Jun. 11-13, 2009. 4 pages.

International Search Report and Written Opinion dated Nov. 20, 2017 in connection with International Application No. PCT/US2017/049024.

Taiwanese Office Action dated Jan. 19, 2018 in connection with Taiwanese Application No. 105139662.

International Preliminary Report on Patentability dated Jun. 14, 2018 in connection with Application No. PCT/US2016/064322.

* cited by examiner

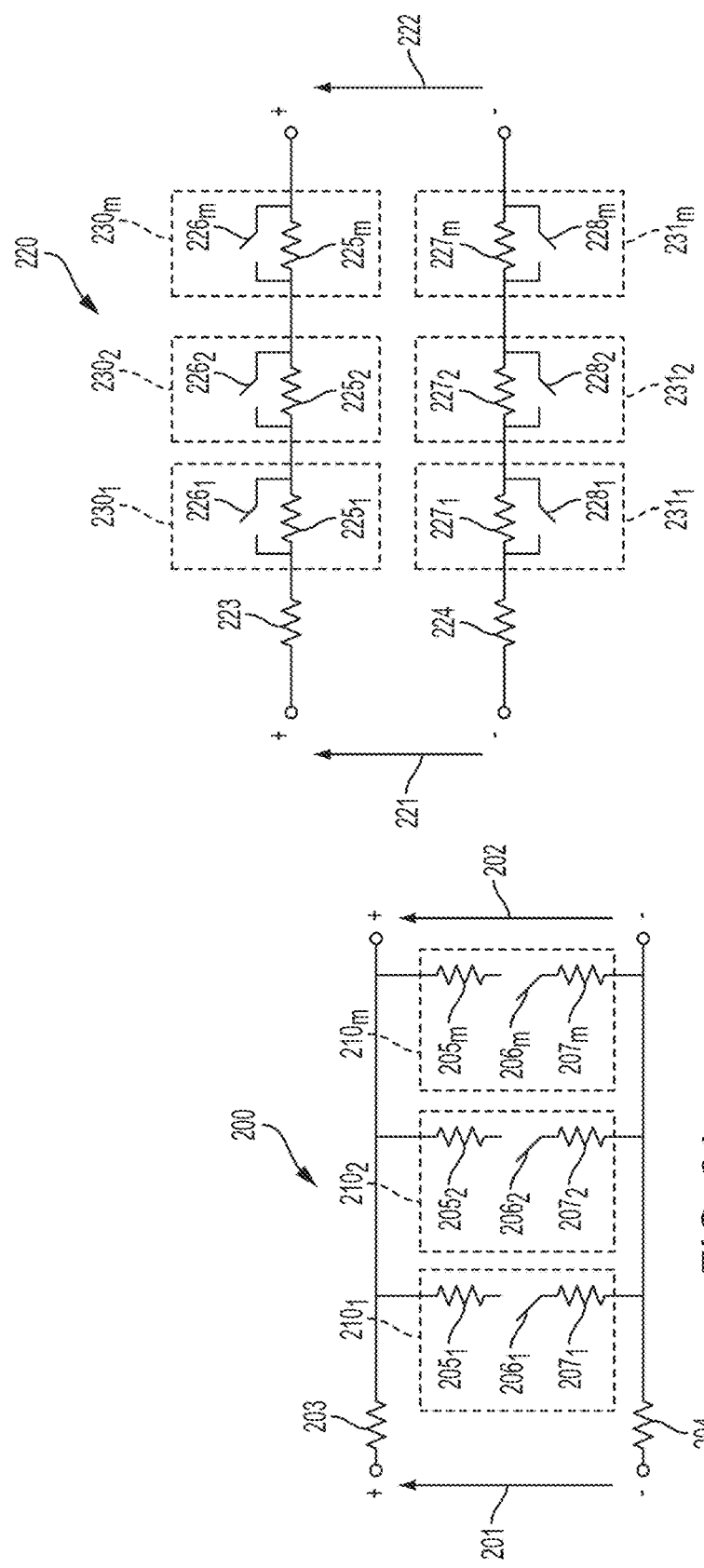

TIME GAIN COMPENSATION CIRCUIT AND RELATED APPARATUS AND METHODS

BACKGROUND

Field

The present application relates to ultrasound devices having a time gain compensation circuit.

Related Art

Ultrasound devices may be used to perform diagnostic imaging and/or treatment. Ultrasound imaging may be used to see internal soft tissue body structures. Ultrasound imaging may be used to find a source of a disease or to exclude any pathology. Ultrasound devices use sound waves with frequencies which are higher than those audible to humans. Ultrasonic images are made by sending pulses of ultrasound into tissue using a probe. The sound waves are reflected off the tissue, with different tissues reflecting varying degrees of sound. These reflected sound waves may be recorded and displayed as an image to the operator. The strength (amplitude) of the sound signal and the time it takes for the wave to travel through the body provide information used to produce an image.

Many different types of images can be formed using ultrasound devices. The images can be real-time images. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

According to an aspect of the present application, there is provided an ultrasound device, comprising a profile generator, an encoder configured to receive a profile signal from the profile generator, and an attenuator configured to receive a signal representing an output of an ultrasound sensor and coupled to the encoder to receive a control signal from the encoder, the attenuator comprising a plurality of binary attenuator stages, the attenuator configured to produce an output signal that is an attenuated version of the input signal.

According to an aspect of the present application, there is provided an ultrasound device, comprising a profile generator, an encoder configured to receive a profile signal from the profile generator, and an attenuator configured to receive a signal representing an output of an ultrasound sensor and coupled to the encoder to receive a control signal from the encoder, the attenuator comprising a plurality of stages, each stage in the plurality of stages having a predetermined attenuation, the attenuator configured to produce an output signal that is an attenuated version of the input signal.

BRIEF DESCRIPTION OF THE DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

FIG. 2A is a circuit diagram illustrating a differential parallel implementation of the attenuator of FIG. 1, according to a non-limiting embodiment of the present application.

FIG. 2B is a circuit diagram illustrating a differential series implementation of the attenuator of FIG. 1, according to a non-limiting embodiment of the present application.

DETAILED DESCRIPTION

The inventors have recognized and appreciated that the power consumption and the accuracy associated with time gain compensation circuits may be improved by replacing variable amplifiers with amplification circuits comprising variable attenuators and fixed gain amplifiers. This approach can significantly simplify the amplifier design shifting the problem from the design of an active circuit to the design of a passive circuit.

Aspects of the present application relate to variable attenuator circuits for time gain compensation comprising a plurality of resistors that are individually digitally enabled. Because the circuits comprise fixed resistors, high degrees of attenuation accuracy, and consequently high degrees of gain accuracy, may be accomplished. Furthermore, the source of power consumption associated with the variable attenuator is the digital circuits enabling the resistors.

The aspects and embodiments described above, as well as additional aspects and embodiments, are described further below. These aspects and/or embodiments may be used individually, all together, or in any combination of two or more, as the application is not limited in this respect.

Figure 1:
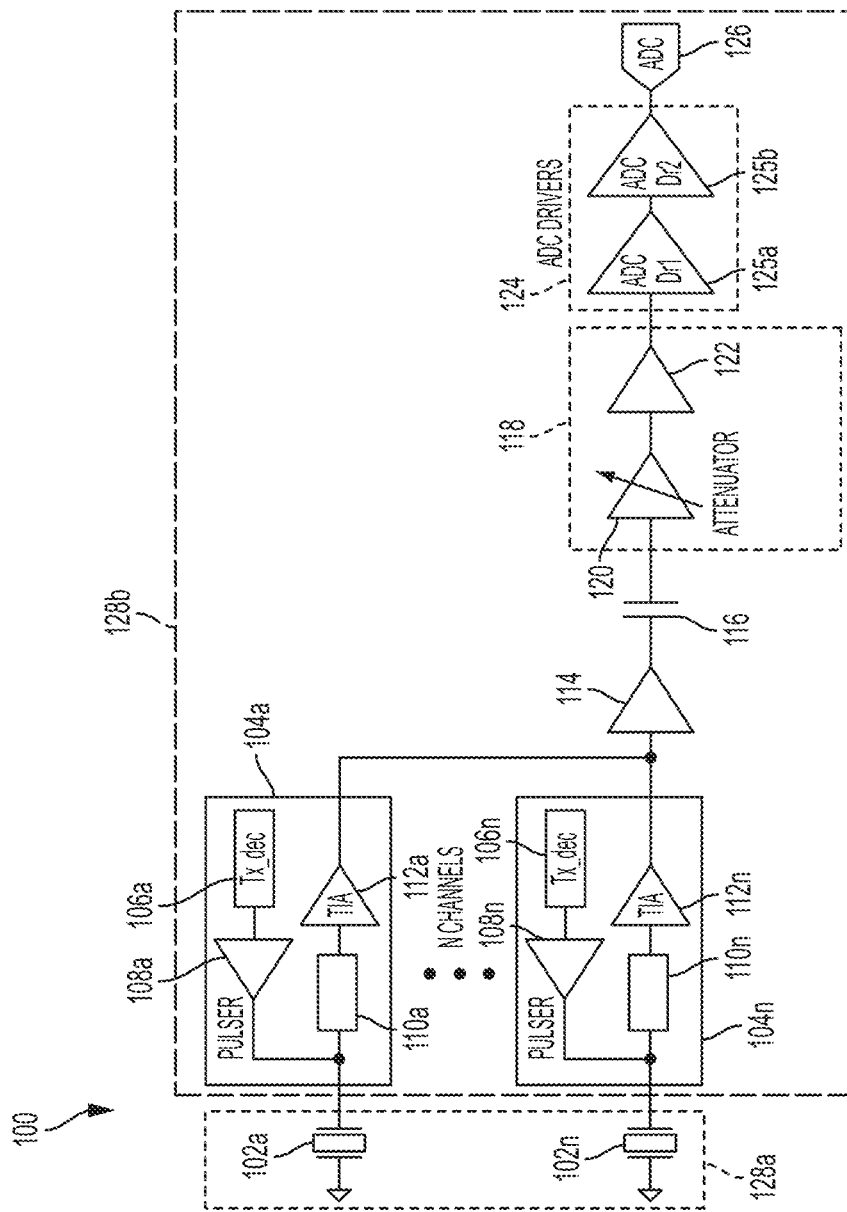
FIG. 1 is a block diagram of an ultrasound device including a time gain compensation circuit, according to a non-limiting embodiment of the present application.

FIG. 1 illustrates a circuit for processing received ultrasound signals, according to a non-limiting embodiment of the present application. The circuit 100 includes N ultrasonic transducers 102a . . . 102n, wherein N is an integer. The ultrasonic transducers are sensors in some embodiments, producing electrical signals representing received ultrasound signals. The ultrasonic transducers may also transmit ultrasound signals in some embodiments. The ultrasonic transducers may be capacitive micromachined ultrasonic transducers (CMUTs) in some embodiments. The ultrasonic transducers may be piezoelectric micromachined ultrasonic transducers (PMUTs) in some embodiments. Further alternative types of ultrasonic transducers may be used in other embodiments.

The circuit 100 further comprises N circuitry channels 104a . . . 104n. The circuitry channels may correspond to a respective ultrasonic transducer 102a . . . 102n. For example, there may be eight ultrasonic transducers 102a . . . 102n and eight corresponding circuitry channels 104a . . . 104n. In some embodiments, the number of ultrasonic transducers 102a . . . 102n may be greater than the number of circuitry channels.

The circuitry channels 104a . . . 104n may include transmit circuitry, receive circuitry, or both. The transmit circuitry may include transmit decoders 106a . . . 106n coupled to respective pulsers 108a . . . 108n. The pulsers 108a . . . 108n may control the respective ultrasonic transducers 102a . . . 102n to emit ultrasound signals.

The receive circuitry of the circuitry channels 104a . . . 104n may receive the electrical signals output from respective ultrasonic transducers 102a . . . 102n. In the illustrated example, each circuitry channel 104a . . . 104n includes a respective receive switch 110a . . . 110n and an amplifier 112a . . . 112n. The receive switches 110a . . . 110n may be controlled to activate/deactivate readout of an electrical signal from a given ultrasonic transducer 102a . . . 102n. More generally, the receive switches 110a . . . 110n may be receive circuits, since alternatives to a switch may be employed to perform the same function. The amplifiers 112a . . . 112n may be trans-impedance amplifiers (TIAs).

The circuit 100 further comprises an averaging circuit 114, which is also referred to herein as a summer or a summing amplifier. In some embodiments, the averaging circuit 114 is a buffer or an amplifier. The averaging circuit 114 may receive output signals from one or more of the amplifiers 112a . . . 112n and may provide an averaged output signal. The averaged output signal may be formed in part by adding or subtracting the signals from the various amplifiers 112a . . . 112n. The averaging circuit 114 may include a variable feedback resistance. The value of the variable feedback resistance may be adjusted dynamically based upon the number of amplifiers 112a . . . 112n from which the averaging circuit receives signals. The averaging circuit 114 is coupled to an auto-zero block 116.

The auto-zero block 116 is coupled to a time gain compensation circuit 118 which includes an attenuator 120 and a fixed gain amplifier 122. Attenuator 120, as well as attenuator 200 of FIG. 2A, attenuator 220 of FIG. 2B, attenuator 240 of FIG. 2C, and attenuator 260 of FIG. 2D, may be a variable attenuator in some embodiments. As will be described further below, one or more resistors may be enabled/disabled thus adjusting the attenuation associated with the attenuator.

The time gain compensation circuit 118 is coupled to an ADC 126 via ADC drivers 124. In the illustrated example, the ADC drivers 124 include a first ADC driver 125a and a second ADC driver 125b. The ADC 126 digitizes the signal(s) from the averaging circuit 114.

While FIG. 1 illustrates a number of components as part of a circuit of an ultrasound device, it should be appreciated that the various aspects described herein are not limited to the exact components or configuration of components illustrated. For example, aspects of the present application relate to the time gain compensation circuit 118.

The components of FIG. 1 may be located on a single substrate or on different substrates. For example, as illustrated, the ultrasonic transducers 102a . . . 102n may be on a first substrate 128a and the remaining illustrated components may be on a second substrate 128b. The first and/or second substrates may be semiconductor substrates, such as silicon substrates. In an alternative embodiment, the components of FIG. 1 may be on a single substrate. For example, the ultrasonic transducers 102a . . . 102n and the illustrated circuitry may be monolithically integrated on the same semiconductor die. Such integration may be facilitated by using CMUTs as the ultrasonic transducers.

According to an embodiment, the components of FIG. 1 form part of an ultrasound probe. The ultrasound probe may be handheld. In some embodiments, the components of FIG. 1 form part of an ultrasound patch configured to be worn by a patient.

The gain of fixed gain amplifier 122 may have values between approximately 1 dB and 100 dB, between approximately 3 dB and 30 dB, between approximately 5 dB and 20 dB, or any other value or range of values. Other values are also possible.

In some embodiments fixed gain amplifier 122 has a gain of 20 dB.

The attenuation of variable attenuator 120 may have values between approximately 1 dB and 100 dB, between approximately 3 dB and 30 dB, between approximately 5 dB and 20 dB, or any other value or range of values. Other values are also possible.

Circuit 200, shown in FIG. 2A, represents a non-limiting embodiment of attenuator 120. Circuit 200 is arranged in a differential configuration. Circuit 200 has a differential input voltage 201 and a differential output voltage 202. Resistor 203 is associated with the "+" side of the differential circuit. On the other hand, series resistors 204 is associated with the "−" side of the differential circuit. Resistor 203 may or may not have a resistance equal to that of resistor 204. Placed in parallel, between the output of resistors 203 and 204 and output voltage 202, are circuits $210_i$, where i may assume values between 1 and m. According to some embodiments, each circuit $210_i$ comprises the series of resistor $205_i$, switch $206_i$ and resistor $207_i$. Resistor $205_i$ may or may not have a resistance equal to that of resistor $207_i$.

Each switch $206_i$ may have 2 possible states: closed or open. When switch $206_i$ is closed, circuit $210_i$ represents a resistor having a resistance equal to the sum of resistors $205_i$ and $207_i$. Contrarily, when switch $206_i$ open, circuit $210_i$ has a resistance equal to infinite. According to some embodiments, the overall resistance seen by the input signal may be varied by changing the state of switches $206_i$. In this configuration, the overall resistance may be defined by a digital code of m bits in length, where a bit equal to 1 represents a closed switch and a bit equal to 0 represents an open switch. Each switch $206_i$ may assume a closed or open state, independently of the state of the other switches.

Resistors 203 and 204, and each resistor $205_i$ and $207_i$ may have values between approximately 1Ω and 10 GΩ, between approximately 100Ω and 100 MΩ, between approximately 1 KΩ and 1 MΩ, or any other value or range of values. Other values are also possible.

In some embodiments, resistors $205_i$ and $207_i$ may be chosen to progressively increase or decrease by a constant factor x as a function of i. For example, if resistor $205_1$ is set to R, resistor $205_2$ may be equal to xR, resistor $205_3$ may be equal to $x^2 R$, and resistor $205_m$ may be equal to $x^{m-1} R$. Factor x may have values between approximately 0.001 and 1000, between approximately 0.1 and 10, between approximately 0.5 and 2, or any other value or range of values. Other values are also possible.

In some embodiments, resistors $205_i$ are all equal to each other and resistors $207_i$ are all equal to each other, for any value of i.

In some embodiments, a fixed attenuation stage may be obtained by closing some or all switches $206_i$ and by setting resistors 203, 204 and each of the resistors $205_i$ and $207_i$ to a predefined value.

Circuit 220, shown in FIG. 2B, represents another non-limiting embodiment of the attenuator 120. Circuit 220 is also arranged in a differential configuration. Circuit 220 has a differential input voltage 221 and a differential output voltage 222. Resistor 223 is associated with the "+" side of the differential circuit. On the other hand, series resistor 224 is associated with the "−" side of the differential circuit. Resistor 223 may or may not have a resistance equal to that of resistor 224. In series to resistor 223 is the series of circuits $230_i$, where i may assume any value between 1 and m. Similarly, in series to resistor 224 is the series of circuits $231_i$. Each circuit $230_i$ comprises resistor $225_i$ configured in parallel to switch $226_i$ and circuit $231_i$ comprises resistor $227_i$ configured in parallel to switch $228_i$. Resistors $225_i$ may or may not have a resistance equal to that of resistor $227_i$.

Each switch $226_i$ and $228_i$ may have 2 possible states: closed or open. According to some embodiments, the overall resistance seen by the input signal may be varied by independently adjusting the state of each switch $226_i$ and $228_i$. As in the parallel circuit described previously, a bit sequence may be used to determine the state of each switch.

Resistors 223 and 224, and each resistor $225_i$ and $227_i$ may have values between approximately 1Ω and 10 GΩ, between approximately 100Ω and 100 MΩ, between approximately 1 KΩ and 1 MΩ, or any other value or range of values. Other values are also possible.

In some embodiments, resistors $225_i$ and $227_i$ may be chosen to progressively increase or decrease by a constant factor x as a function of i. For example, if resistor $225_1$ is set to R, resistor $225_2$ may be equal to xR, resistor $225_3$ may be equal to $x^2R$, and resistor $225_m$ may be equal to $x^{m-1}R$. Factor x may have values between approximately 0.001 and 1000, between approximately 0.1 and 10, between approximately 0.5 and 2, or any other value or range of values. Other values are also possible.

In some embodiments, resistors $225_i$ are all equal to each other and resistors $227_i$ are all equal to each other, for any value of i.

In some embodiments, a fixed attenuation stage may be obtained by closing some or all switches $226_i$ and $228_i$ and by setting resistors 223, 224 and each of the resistors $225_i$ and $227_i$ to a predefined value.

While circuit 200 represents a differential parallel embodiment of attenuator 120, circuit 220 represents a differential series embodiment of attenuator 120. As may be appreciated by a person of ordinary skills in the art, any suitable combination of parallel and series arrangements may be used.

Figure 2C:
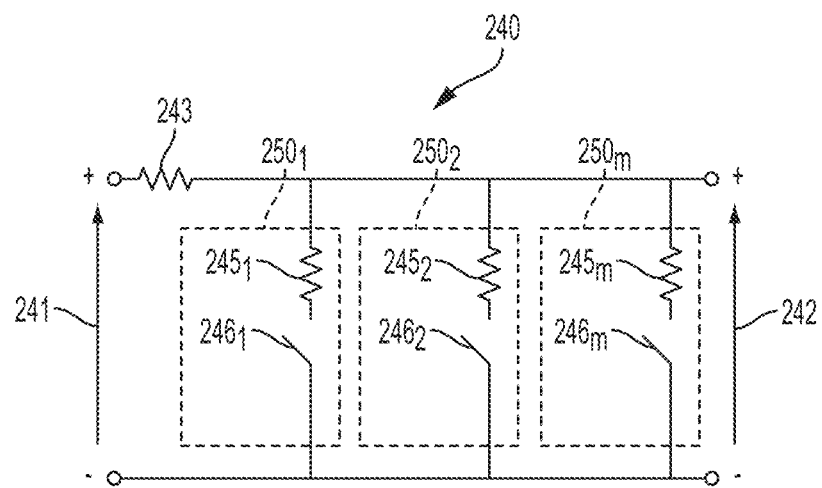
FIG. 2C is a circuit diagram illustrating a single-ended parallel implementation of the attenuator of FIG. 1, according to a non-limiting embodiment of the present application.

Circuit 240, shown in FIG. 2C, represents another non-limiting embodiment of the attenuator 120. Circuit 240 is arranged in a single-ended configuration, as the—side of the circuit is connected to ground. Circuit 240 has a single-ended input voltage 241 and a single-ended output voltage 242. Circuit 240 comprises series resistor 243, and parallel circuits $250_i$, where i may assume any value between 1 and m. Each circuit $250_i$ comprises resistor $245_i$ connected in series to switch $246_i$.

Each switch $246_i$ may have 2 possible states: closed or open. According to some embodiments, the overall resistance seen by the input signal may be varied by independently adjusting the state of each switch $246_i$. As in the parallel circuits described previously, a bit sequence may be used to determine the state of each switch.

Resistors 243, and each resistor $245_i$ may have values between approximately 1Ω and 10 GΩ, between approximately 100Ω and 100 MΩ, between approximately 1 KΩ and 1 MΩ, or any other value or range of values. Other values are also possible.

In some embodiments, resistors $245_i$ may be chosen to progressively increase or decrease by a constant factor x as a function of i. For example, if resistor $245_1$ is set to R, resistor $245_2$ may be equal to xR, resistor $245_3$ may be equal to $x^2R$, and resistor $245_m$ may be equal to $x^{m-1}R$. Factor x may have values between approximately 0.001 and 1000, between approximately 0.1 and 10, between approximately 0.5 and 2, or any other value or range of values. Other values are also possible.

In some embodiments, resistors $245_i$ are all equal to each other.

In some embodiments, a fixed attenuation stage may be obtained by closing each switch $246_i$ and by setting resistors 243 and each of the resistors $245_i$ to a predefined value, for any value of i.

Figure 2D:
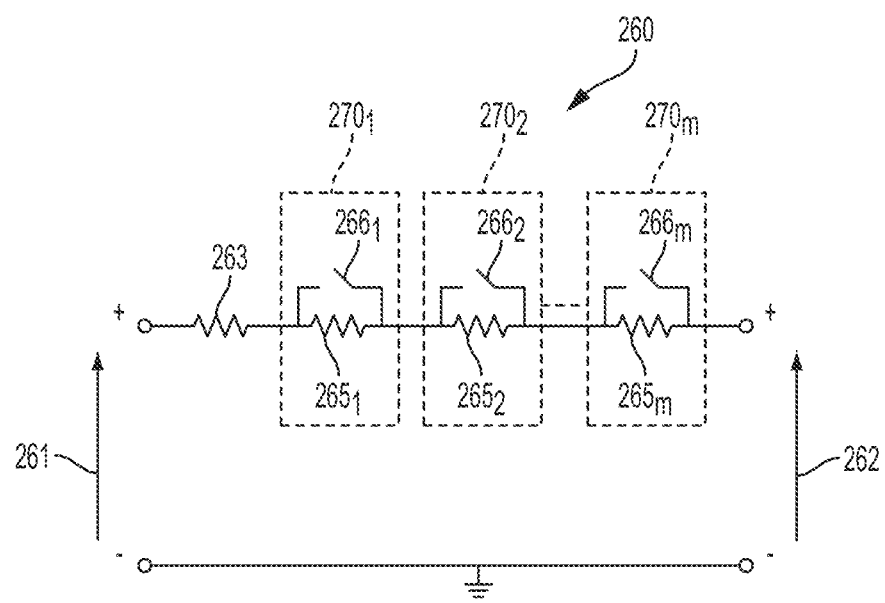
FIG. 2D is a circuit diagram illustrating a single-ended series implementation of the attenuator of FIG. 1, according to a non-limiting embodiment of the present application.

Circuit 260, shown in FIG. 2D, represents another non-limiting embodiment of the attenuator 120. Circuit 260 is also arranged in a single-ended configuration. Circuit 260 has a single-ended input voltage 261 and a single-ended output voltage 262. Circuit 260 comprises series resistor 263 connected in series to circuits $270_i$, where i may assume any value between 1 and m. Each circuit $270_i$ comprises resistor $265_i$ connected in parallel to switch $266_i$.

Each switch $266_i$ may have 2 possible states: closed or open. According to some embodiments, the overall resistance seen by the input signal may be varied by independently adjusting the state of each switch $266_i$. As in the parallel circuits described previously, a bit sequence may be used to determine the state of each switch.

Resistors 263, and each resistor $265i$ may have values between approximately 1Ω and 10 GΩ, between approximately 100Ω and 100 MΩ, between approximately 1 KΩ and 1 MΩ, or any other value or range of values. Other values are also possible.

In some embodiments, resistors $265_i$ may be chosen to progressively increase or decrease by a constant factor x as a function of i. For example, if resistor $265_1$ is set to R, resistor $265_2$ may be equal to xR, resistor $265_3$ may be equal to $x^2R$, and resistor $265_m$ may be equal to $x^{m-1}R$. Factor x may have values between approximately 0.001 and 1000, between approximately 0.1 and 10, between approximately 0.5 and 2, or any other value or range of values. Other values are also possible.

In some embodiments, resistors $265_i$ are all equal to each other.

According to some embodiments, a fixed attenuation stage may be obtained by closing some or all switches $266_i$ and by setting resistors 263 and each of the resistors $265_i$ to a predefined value, for any value of i.

While circuit 240 represents a single-ended parallel embodiment of attenuator 120, circuit 260 represents a single-ended series embodiment of attenuator 120. As may be appreciated by a person of ordinary skills in the art, any suitable combination of parallel and series arrangements may be used.

Figure 3:
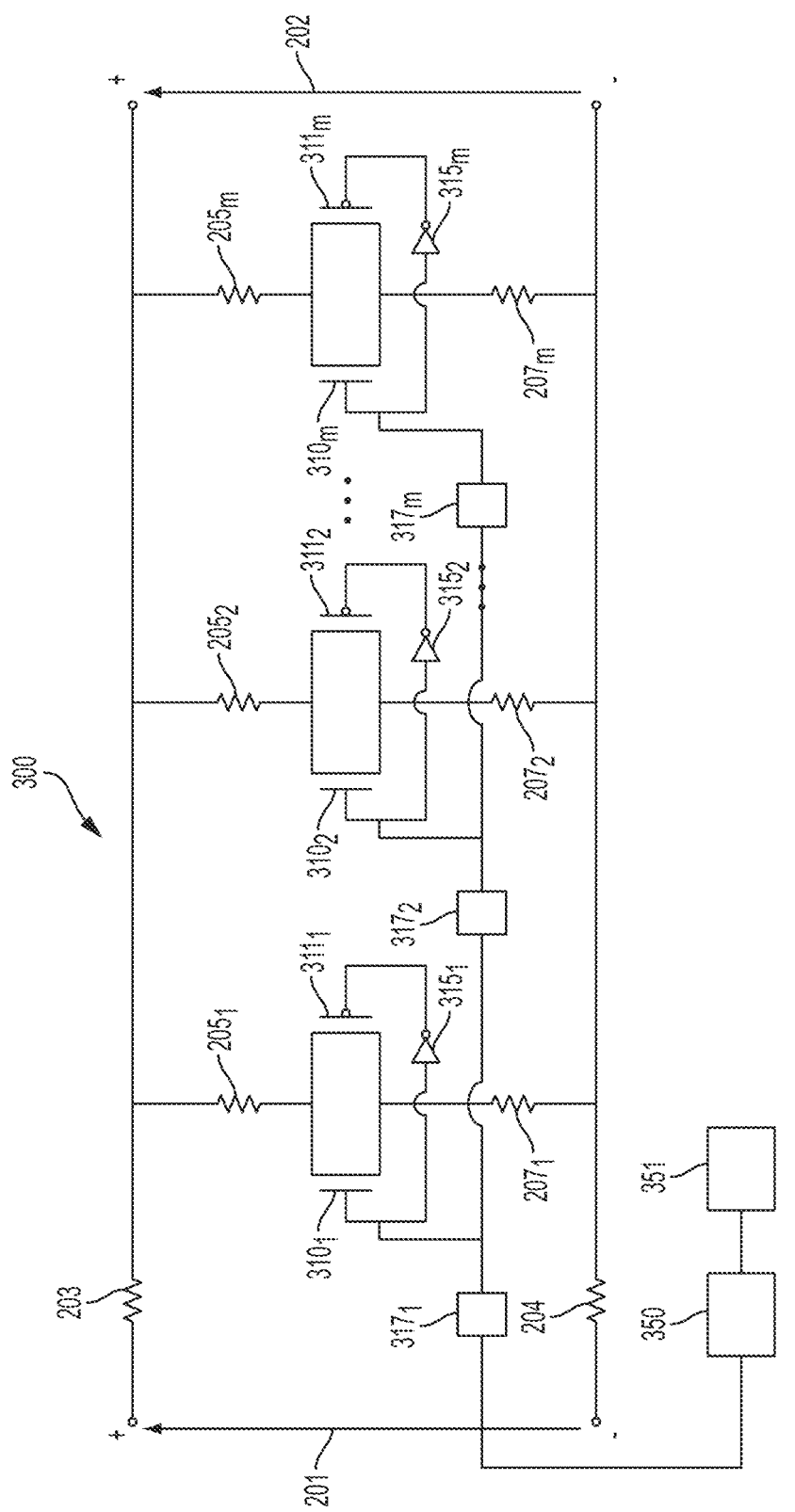
FIG. 3 is a circuit diagram illustrating an implementation of the attenuator of FIG. 1, including complementary switches, according to a non-limiting embodiment of the present application.

FIG. 3 shows a non-limiting embodiment of attenuator 120. While circuit 300 is presented in a differential parallel configuration, other configurations may be used. For example a differential series configuration or a single-ended parallel configuration or a single-ended series configuration or any other suitable combination thereof may be used. According to some non-limiting aspects of the present application, switched $206_i$ may be implemented by complementary switches as shown in FIG. 3. The complementary switches may comprise a nMOS transistor $310_i$ and a pMOS transistor $311_i$. The drain of nMOS transistor $310_i$ may be connected to the source of pMOS transistor $311_i$. The source of nMOS transistor $310_i$ may be connected to the drain of pMOS transistor $311_i$. The gate of nMOS transistor $310_i$ may be connected to the input port of inverter $315_i$ whose output port may be connected to the gate of pMOS transistor $311_i$.

As may readily be appreciated by a person of ordinary skill in the art, while FIG. 3 shows complementary switches based on one pMOS transistor and one nMOS transistor, any suitable number of pMOS transistors and nMOS transistors may be used. In addition, a non-complementary switch using only nMOS (or only pMOS) transistors may be used.

As may further be appreciated by a person of ordinary skill in the art, while FIG. 3 shows complementary switches based on metal-oxide-semiconductor (MOSFET) transistors, any other type of transistors may be used. Transistors $310_i$ and $311_i$ may be implemented by BJT, BiCMOS, JFET, IGFET, MESFET or any other suitable type of transistor.

In some embodiments, flip-flops $317_i$, where i may assume any value between 1 and m, may be used to set the state of complementary switches $206_i$. The output port of each flip-flop $317_i$ may be connected to the gate of each nMOS transistor $310_i$. As further described below, in some embodiments, instead of connecting the gates of the two transistors through inverters $315_i$, the Q port of each flip-flop $317_i$ may be connected to the gate of each nMOS transistor $310_i$ while the $\overline{Q}$ (Q not) port of each flip-flop $317_i$ may be connected to the gate of each pMOS transistor $311_i$. Furthermore, the output port of each flip-flop $317_i$ may be connected to the input port of the following flip-flop $317_{i+1}$, where i may assume any value between 1 and m-1. According to some aspects of the present application, flip-flops $317_i$ collectively represent a shift register.

In some embodiments, flip-flops $317_i$ may be controlled by encoder 350. In turn, encoder 350 may be controlled by profile generator 351. According to some aspects of the present application, profile generator 351 may be a circuit that generates a target time gain compensation response and sources the control signals necessary to track the desired profile. The target time gain compensation response may be manually defined by a user, automatically defined by a computer, or defined in any other suitable manner.

Figure 4:
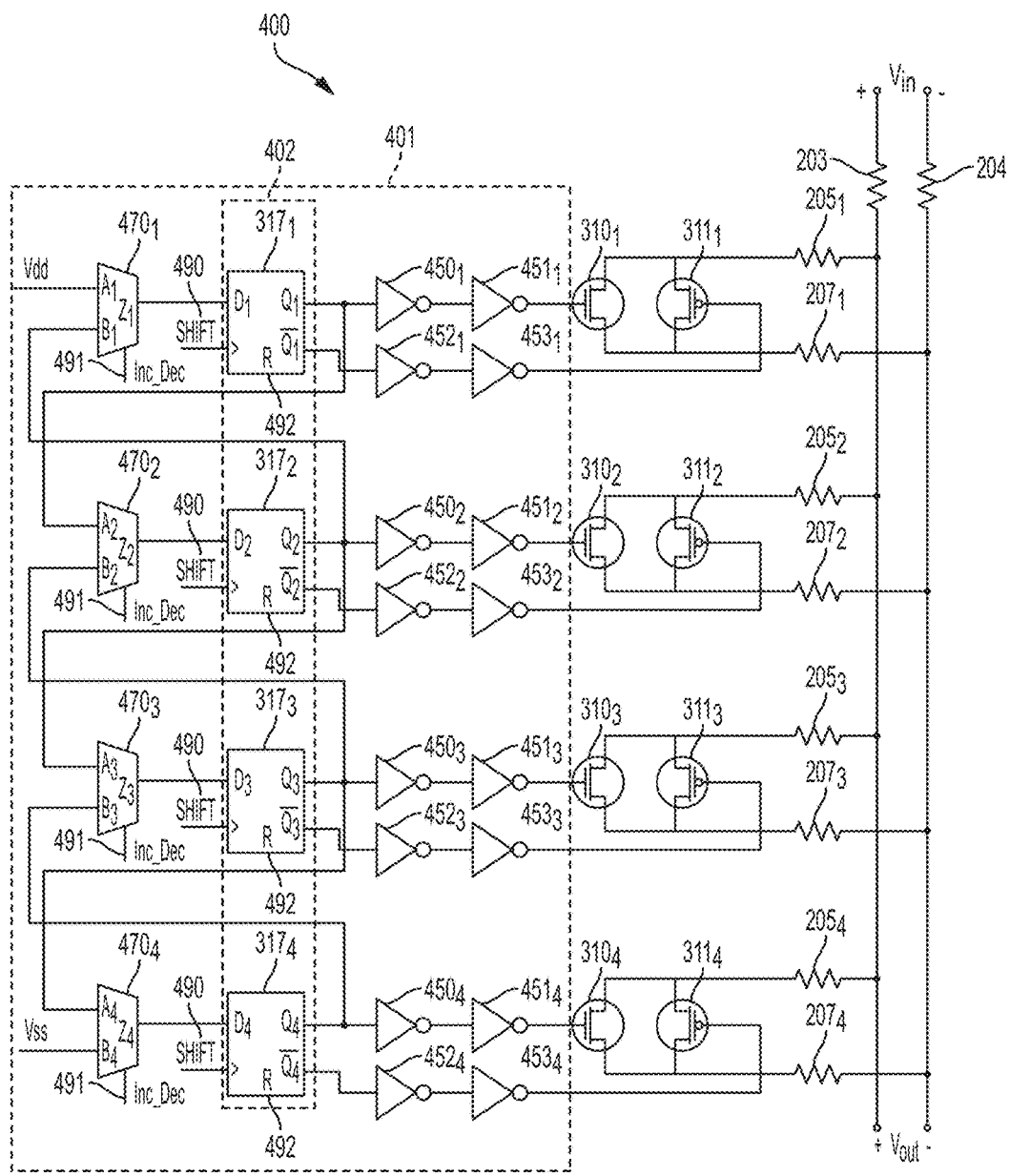
FIG. 4 is a circuit diagram illustrating the digital encoder and shift register used to determine the state of the complementary switches of FIG. 3, according to a non-limiting embodiment of the present application.

FIG. 4 shows a non-limiting embodiment of attenuator circuit 300. While attenuator 400 comprises four attenuation stages each corresponding to one complementary switch, any other suitable number of stages may be used. According to some aspects of the present application, within circuit 400 is digital circuit 401. In the non-limiting example, digital circuit 401 comprises four 2-to-1 multiplexers $470_i$, a shift register 402 consisting of four flip-flops $317_i$ (also illustrated in FIG. 3), four inverter pairs $450_i$ and $452_i$ and four inverter pairs $453_i$ and $454_i$. At any moment in time each flip-flops $317_i$ may be set to a 1 or 0 state through input port D. When flip-flop $317_i$ is triggered by shift signal 490, output port $Q_i$ is set to the same value as $D_i$, while output port $\overline{Q}_i$ is set to the opposite value. In some embodiments flip-flop $317_i$ may be triggered by a rising edge or a falling edge. In some other embodiments flip-flop $317_i$ may be triggered by a 1 pulse or by a 0 pulse. Reset signal 492 may be used to set the state of all flip-flops to 0. Each port $Q_i$ may be connected to the gate of each nMOS transistor $310_i$ through an inverter pair $450_i$ and $451_i$. Similarly, each port $\overline{Q}_i$ may be connected to the gate of each pMOS transistor $311_i$ through an inverter pair $451_i$ and $452_i$. Inverter pairs may be used to prevent undesired voltage spikes from hitting the complementary switches.

In some embodiments, 2-to-1 multiplexers $470_i$ may be used to set the state of each bit of shift register 402. Each multiplexer $470_i$ may have two input ports $A_i$ and $B_i$ and one output port $Z_i$. When the value of the Inc_Dec is set to 0, $Z_i$ may assume the value of $A_i$, independently of the value of $B_i$. Contrarily, when the value of the Inc_Dec is set to 1, $Z_i$ may assume the value of $B_i$, independently of the value of $A_i$. However any other suitable logic may be used. In some embodiments, ports $A_1$ and $B_4$ may be set by the profile generator, while all other port $A_i$ and $B_i$ are set by the output Q of the neighboring flip-flop. In a non-limiting example, $A_i$ may be set by $Q_{i-1}$ and $B_i$ may be set by $Q_{i+1}$.

In some embodiments, when Inc_Dec signal 491 is set to 0 and the register is triggered by shift signal 490, the bits stored in the register may shift from the least significant flip-flop $317_1$ to the most significant flip-flop $317_4$. Contrarily, when Inc_Dec is set to 1 and the register is triggered by shift signal 490, the bits stored in the register may shift from the most significant flip-flop $317_4$ to the least significant flip-flop $317_1$.

Figure 5:
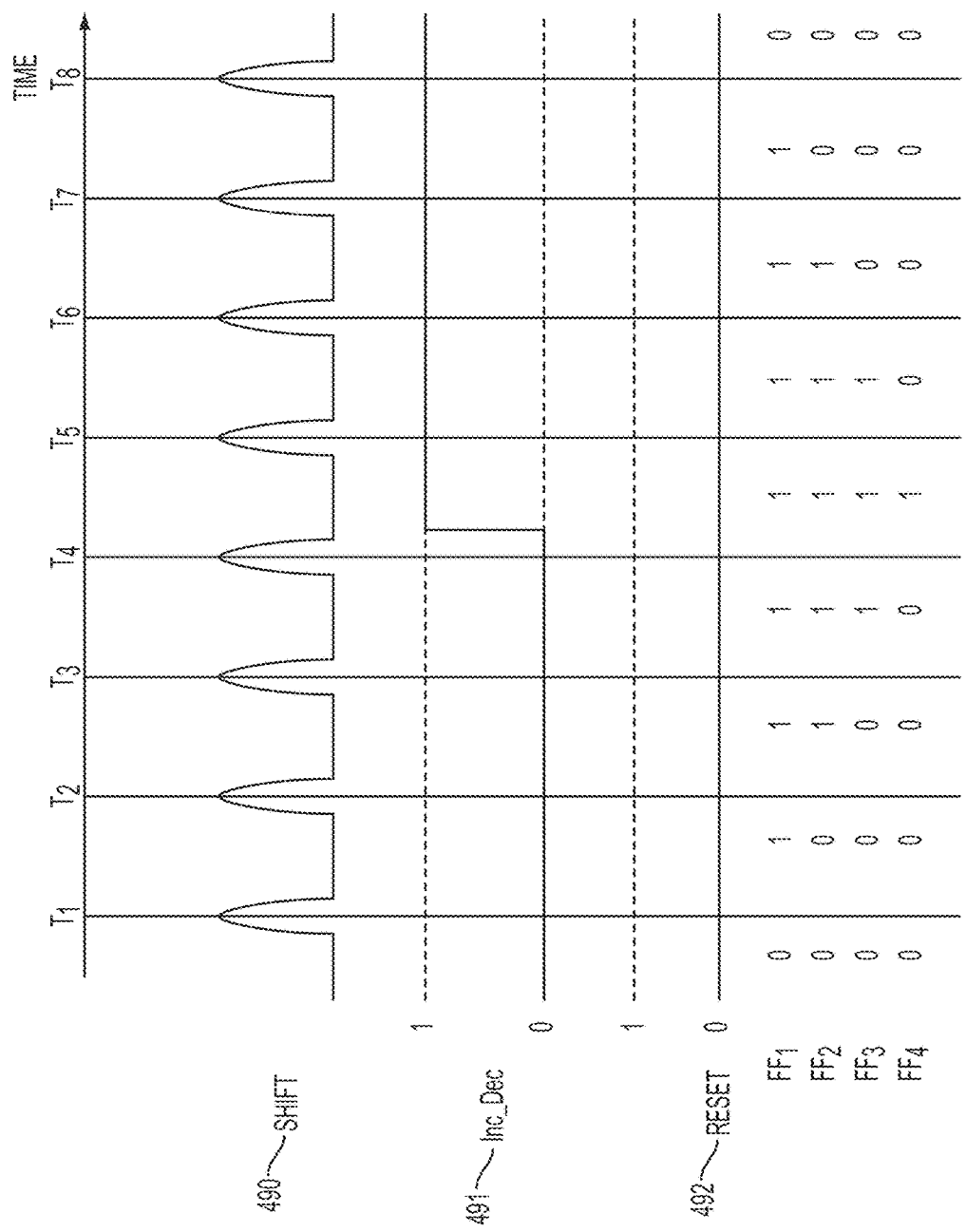
FIG. 5 is a graph illustrating the temporal evolution of three control signals and the state of the shift register of FIG. 4, according to a non-limiting embodiment of the present application.

FIG. 5 shows a non-limiting example of operation of digital circuit 401. The top portion of the chart shows three control signals: shift signal 490, Inc_Dec signal 491 and Reset signal 492. The bottom portion of the chart shows the state of each flip-flop of the shift register in response to the three control signals, where $FF_i$ represents flip-flop $317_i$ of FIG. 4. From $T_1$ through $T_4$, in response to the control signal Inc_Dec being set to 0, the register shifts bits towards $FF_4$. The shift occurs when the circuit is triggered by shift signal 490. From $T_5$ through $T_8$, in response to the control signal Inc_Dec being set to 1, the register shifts bits towards $FF_1$. While in the non-limiting example Reset is set to 0 at all times, it may be set to 1 at any time thus setting the state of each flip-flop to 0.

Figure 6:
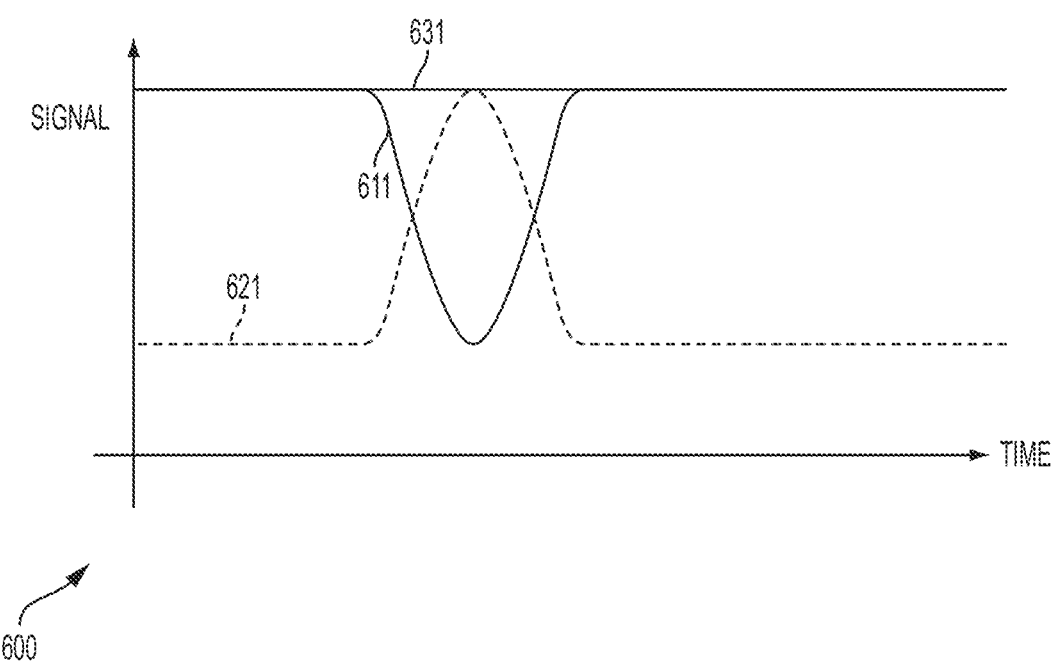
FIG. 6 is a graph illustrating a time gain compensation response triggered by the reception of a signal featuring a dip, according to a non-limiting embodiment of the present application.

FIG. 6 shows a non-limiting example of a time-dependent response generated by the time gain compensation circuit 118, which may comprise variable attenuator 120 and fixed gain amplifier 122. Chart 600 shows three signals as a function of time. Curve 611 shows the response received by one or more transducers $102_i$, obtained by sending an ultrasonic wave towards a target. The target may comprise multiple layers, causing multiple reflections having varying magnitude as a function of depth. Curve 611 shows a dip that may be caused by a multilayered target. In some embodiments, in order to obtain a clear ultrasound image it may be desirable to have a uniform response as a function of time as shown by curve 631. Consequently, profile generator 351 may source control signals so as to provide a gain response that compensates losses caused by the depth-dependent reflections. Curve 621 is a non-limiting example of such gain response.

In some embodiments, each binary attenuation stage can provide about 0.2 dB of attenuation.

In some other embodiments, it may be desirable to generate a gain response that causes the compensated signal to have any suitable time-dependent behavior. For example, in order to improve the contrast of an ultrasound image, it may be desirable to magnify the response of one layer of the target while attenuating the response of another layer. The time gain compensation response may be manually defined by the user, automatically defined by a computer, or defined in any other suitable manner.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. It is, therefore, to be understood that the foregoing embodiments are presented by way of example only and that, within the scope of the appended claims and equivalents thereto, inventive embodiments may be practiced otherwise than as specifically described.

As described, some aspects may be embodied as one or more methods. The acts performed as part of the method(s) may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The phrase "and/or," as used herein in the specification and in the claims, should be understood to mean "either or both" of the elements so conjoined, i.e., elements that are conjunctively present in some cases and disjunctively present in other cases.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements.

As used herein, the term "between" used in a numerical context is to be inclusive unless indicated otherwise. For example, "between A and B" includes A and B unless indicated otherwise.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. An ultrasound device, comprising:
   a profile generator;
   an encoder configured to receive a profile signal from the profile generator;
   an attenuator configured to receive an input signal representing an output of an ultrasound sensor and coupled to the encoder to receive a control signal from the encoder, the attenuator comprising a plurality of binary attenuator stages, the attenuator configured to produce an output signal that is an attenuated version of the input signal; and
   a fixed gain amplifier having a gain greater than 0 dB and configured to receive the output signal from the attenuator and amplify the output signal.

2. The ultrasound device of claim 1, wherein the profile generator provides a target attenuation profile.

3. The ultrasound device of claim 1, wherein each of the plurality of binary attenuation stages provides about 0.2 dB of attenuation.

4. The ultrasound device of claim 1, wherein each of the plurality of binary attenuation stages comprises at least one complementary switch.

5. The ultrasound device of claim 1, wherein each of the plurality of binary attenuation stages is single-ended.

6. The ultrasound device of claim 1, wherein each of the plurality of binary attenuation stages is differential.

7. The ultrasound device of claim 1, wherein the plurality of binary attenuation stages are connected in parallel to form the attenuator.

8. The ultrasound device of claim 1, wherein the plurality of binary attenuation stages are connected in series to form the attenuator.

9. The ultrasound device of claim 1, wherein the plurality of binary attenuation stages are connected in series and parallel to form the attenuator.

10. An ultrasound device, comprising:
    a profile generator;
    an encoder configured to receive a profile from the profile generator;
    an attenuator configured to receive an input signal representing an output of an ultrasound sensor and coupled to the encoder to receive a control signal from the encoder, the attenuator comprising a plurality of stages, each stage in the plurality of stages having a predetermined attenuation, the attenuator configured to produce an attenuated output signal that is an attenuated version of the input signal; and
    a fixed gain amplifier having a gain greater than 0 dB and configured to receive the output signal from the attenuator and amplify the output signal.

11. The ultrasound device of claim 10, wherein the profile generator provides a target attenuation profile.

12. The ultrasound device of claim 10, wherein each of the plurality of stages provides about 0.2 dB of attenuation.

13. The ultrasound device of claim 10, wherein each of the plurality of stages comprises at least one complementary switch.

14. The ultrasound device of claim 10, wherein each of the plurality of stages is single-ended.

15. The ultrasound device of claim 10, wherein each of the plurality of stages is differential.

16. The ultrasound device of claim 10, wherein the plurality of stages are connected in parallel to form the attenuator.

17. The ultrasound device of claim 10, wherein the plurality of stages are connected in series to form the attenuator.

18. The ultrasound device of claim 10, wherein the plurality of stages are connected in series and parallel to form the attenuator.

19. The ultrasound device of claim 1, wherein the fixed gain amplifier has a gain between approximately 1 dB and 100 dB.

20. The ultrasound device of claim 1, wherein the attenuator and the fixed gain amplifier are configured to perform time-gain compensation on the input signal.

21. The ultrasound device of claim 10, wherein the fixed gain amplifier has a gain between approximately 1 dB and 100 dB.

22. The ultrasound device of claim 10, wherein the attenuator and the fixed gain amplifier are configured to perform time-gain compensation on the input signal.

* * * * *